(12) United States Patent
Giraldo et al.

(10) Patent No.: US 7,098,788 B2
(45) Date of Patent: Aug. 29, 2006

(54) REMOTE SURVEILLANCE AND ASSISTED CARE USING A MOBILE COMMUNICATION DEVICE

(75) Inventors: Carlos M. Giraldo, Gainesville, FL (US); Abdelsalam A. Helal, Gainesville, FL (US); Youssef Omar Kaddoura, Gainesville, FL (US); William C. Mann, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 97 days.

(21) Appl. No.: 10/889,162

(22) Filed: Jul. 12, 2004

(65) Prior Publication Data

US 2005/0057361 A1 Mar. 17, 2005

Related U.S. Application Data

(60) Provisional application No. 60/490,717, filed on Jul. 29, 2003, provisional application No. 60/486,018, filed on Jul. 10, 2003.

(51) Int. Cl.
*G08B 1/08* (2006.01)

(52) U.S. Cl. .......................... 340/539.25; 340/539.13; 340/825.19; 340/825.36; 340/825.49

(58) Field of Classification Search .......... 340/539.25, 340/539.13, 565, 573.4, 825.19, 825.36, 340/825.49; 348/14.16, 14.01
See application file for complete search history.

(56) References Cited

U.S. PATENT DOCUMENTS

| | | | |
|---|---|---|---|
| 5,546,072 A * | 8/1996 | Creuseremee et al. ...... 340/574 |
| 5,801,618 A * | 9/1998 | Jenkins ................. 340/426.14 |
| 5,833,603 A | 11/1998 | Kovacs et al. |
| 5,844,599 A * | 12/1998 | Hildin ....................... 348/14.1 |
| 5,872,834 A | 2/1999 | Teitelbaum |
| 6,204,763 B1 | 3/2001 | Sone |
| 6,243,683 B1 * | 6/2001 | Peters ....................... 704/273 |
| 6,362,778 B1 | 3/2002 | Neher |
| 6,380,858 B1 | 4/2002 | Yarin et al. |
| 6,404,880 B1 | 6/2002 | Stevens |
| 6,428,475 B1 | 8/2002 | Shen |
| 6,453,027 B1 | 9/2002 | Kang et al. |
| 6,496,111 B1 | 12/2002 | Hosack |
| 6,553,262 B1 | 4/2003 | Lang et al. |
| 6,567,672 B1 | 5/2003 | Park et al. |
| 6,678,516 B1 | 1/2004 | Nordman et al. |
| 6,774,795 B1 | 8/2004 | Eshelman et al. |
| 6,965,294 B1 * | 11/2005 | Elliott et al. ................. 340/5.2 |
| 2001/0046862 A1 | 11/2001 | Coppinger et al. |
| 2002/0060243 A1 | 5/2002 | Janiak et al. |
| 2002/0127145 A1 | 9/2002 | Der Ghazarian et al. |
| 2002/0128864 A1 | 9/2002 | Maus et al. |
| 2003/0009088 A1 | 1/2003 | Korth et al. |
| 2003/0013507 A1 | 1/2003 | Sato |

(Continued)

OTHER PUBLICATIONS

Mann, W., et al., "Smart Phones for the Elders: Boosting the Intelligence of Smart Homes", Am. Assoc. for Artifical Intell. (AAAI), (Jul. 2002).

(Continued)

*Primary Examiner*—Daryl C Pope
(74) *Attorney, Agent, or Firm*—Akerman Senterfitt (57) ABSTRACT

A method of remote surveillance and assisted care using a mobile communication device can include determining a location of a user. The method can also include adjusting at least one camera according to the location, and capturing an image of an area around the location. Further, the method can include transmitting the image to a remote information processing system.

10 Claims, 3 Drawing Sheets

U.S. PATENT DOCUMENTS

| | | |
|---|---|---|
| 2003/0064732 A1 | 4/2003 | McDowell et al. |
| 2003/0064749 A1 | 4/2003 | Soini et al. |
| 2003/0083020 A1 | 5/2003 | Langford |
| 2003/0087628 A1 | 5/2003 | Michibata |

OTHER PUBLICATIONS

Haigh, K., et al., "The Role of Intelligent Technology in Elder Care", AAAI-02 WS on Automation as Caregiver, (Jul. 2002).

Giraldo, C., "mPCA-A Mobile Patient Care-Giving Assistant for Alzheimer Patients", UbiCog '02, (Sep. 29, 2002).

Helal, S., et al., "Smart Phone Based Cognitive Assistant", UbiHealth, (Oct. 12-15, 2003).

Helal, S., et al., "Assistive Environments for Successful Aging". UbiComp 2003, (2003).

Helal, S., et al., "Enabling Location-Aware Pervasive COmputing Applications for the Elderly", IEEE Conf. on Pervasive Computing & Comm. PerCom '03, (2003).

Helal, S., et al., "Assistive Environments for Elder Care—Integrating Smart Phones with Smart Homes", ICADI Conf. on Aging, (2003).

Long, M., "A New Reference Design for Jumpstarting Smartphone Development", E-inSITE, (Feb. 13, 2003).

"Home Automation Systems", National Security, Inc., Internet, viewed (Jun. 3, 2003).

"SmartPhones", Motorola, Internet, (viewed Jun. 3, 2003).

"An Executive White Paper—Secure Mobile Banking Architecture", Consumer Direct Link, Inc., (Sep. 2001).

Paron MPC, Consumer Direct Link, Inc., (2000-2001).

* cited by examiner

REMOTE SURVEILLANCE AND ASSISTED CARE USING A MOBILE COMMUNICATION DEVICE

CROSS-REFERENCE TO RELATED APPLICATIONS

This application claims the benefit of both U.S. Provisional Application No. 60/486,018, filed in the United States Patent and Trademark Office on Jul. 10, 2003, and U.S. Provisional Application No. 60/490,717 filed in the United States Patent and Trademark Office on Jul. 29, 2003, the entirety of both applications which is incorporated herein by reference.

BACKGROUND

1. Field of the Invention

The invention relates to the field of mobile communications and, more particularly, to the use of a mobile communication device to provide remote surveillance and assisted care functions.

2. Description of the Related Art

Individuals suffering from physical or mental challenges, such as elderly persons, commonly require a caregiver to provide assistance with daily activities. However, in cases where the elderly person is high functioning and desires to maximize independence, a fulltime, onsite caregiver can be unnecessary, costly, and/or intrusive. Thus, the elder may require a remote caregiver who can assist the elder only when the elder asks for, or requires, help.

Conventional methods of providing remote care giving typically employ the use of portable communication devices. However, typical portable communication devices, such as pagers and cell phones, are limited. For example, in the case of a paging device, the elder must wait for a call back from the caregiver. Similarly, in the case of a cell phone, the caregiver may be out of range or unavailable, requiring the elder to leave a message and wait until the caregiver responds.

A further shortcoming of conventional remote care giving is the inability of the caregiver to make an immediate visual assessment of the elder's condition. For instance, in order to determine the elder's condition upon receiving a request for help, the caregiver must typically converse with the elder telephonically, which can be problematic if the elder is unable to speak or physically get to a phone. Further, the caregiver often must physically travel to the location of the elder to determine the nature of the help request, which can delay necessary treatment for the elder. The inability of the caregiver to have immediate knowledge of the elder's condition may result in the caregiver underestimating the gravity of the elder's condition. Conversely, the caregiver may overestimate the severity of the elder's condition, which may result in unnecessary and costly calls to emergency personnel, such as the fire department, ambulance, or the like.

Additionally, an elder may need a caregiver to unobtrusively check in on the elder from time to time. Optimally, the caregiver should be able to observe the elder without causing a disruption in the elder's day. However, conventional human surveillance mechanisms have many shortcomings. For example, typical remote viewing mechanisms, such as a monitor or dedicated display screen, are not portable and are operable only at a fixed location.

What is needed is a remote surveillance and assisted care device for cognitively impaired individuals, such as the elderly.

SUMMARY OF THE INVENTION

The present invention provides a method, a system, and an apparatus for providing remote surveillance and assisted care functionality within a defined space using a mobile communication device, such as a mobile telephone. More specifically, a mobile communication device can allow a user, such as a person suffering from physical or mental challenges, to communicate with a smart space control module. The smart space control module can be configured to determine the location of the mobile communication device, and orient one or more cameras to focus on the mobile communication device, thereby tracking the mobile communication device's movements. Since the mobile communication device can be located on or near the body of the user, the cameras can effectively follow the user as he or she travels within the defined space.

The user can send a help request to the smart space control module using the mobile communication device. Accordingly, the smart space control module can identify the help request using speech recognition, and forward the help request to a remote information processing system, such as a mobile communication device, which can be configured for operation by a remote agent, such as a caregiver. Upon receiving the help request, the caregiver can send a request to the smart space control module to obtain a digital photo of the user to be displayed on the remote information processing system. Additionally, a caregiver can access views obtained from the cameras connected to the smart space control module via the Internet in order to observe the user in real-time.

One aspect of the present invention can include a method of remote surveillance and assisted care using a mobile communication device. The method can include determining a location of a user, adjusting at least one camera according to the location, and capturing an image of an area around the location. The method also can include transmitting the image to a remote information processing system.

The method can also include receiving within the mobile communication device a spoken utterance, and transmitting the spoken utterance to a voice recognition engine. In one embodiment, the transmitting step can include transmitting the spoken utterance over a short range wireless network.

Another aspect of the present invention can include receiving the utterance from the mobile communication device, converting the utterance into text, and identifying at least a portion of the text as a help request. The method can include transmitting the help request to the remote information processing system. The method can also include, prior to the step of determining a location of the mobile communication device, receiving from the remote information processing system a status request to view the image.

Yet another aspect of the present invention can include a system for providing remote surveillance. The system can include a location tracking mechanism and a mobile communication device configured to interact with the location tracking mechanism. The system also can include a server in communication with the location tracking mechanism and the mobile communication device. Further, the system can include at least one adjustable camera. Accordingly, the server can be configured to control the orientation of the adjustable camera based upon information from the location tracking system.

In one embodiment, the server can further include a voice recognition engine. Accordingly, the server can receive a user utterance from the mobile communication device, and convert the user utterance into text. The server can also identify the user utterance as a request for help and responsively contact a caregiver. In another embodiment, the voice recognition engine can be disposed within a personal computer. In yet another embodiment, the server can obtain an image from at least one adjustable camera, and can transmit the image to a remote information processing system.

Other embodiments of the present invention can include a machine readable storage for causing a machine to perform the steps described herein.

BRIEF DESCRIPTION OF THE DRAWINGS

There are shown in the drawings, embodiments that are presently preferred; it being understood, however, that the invention is not limited to the precise arrangements and instrumentalities shown.

DETAILED DESCRIPTION OF THE INVENTION

Figure 1:
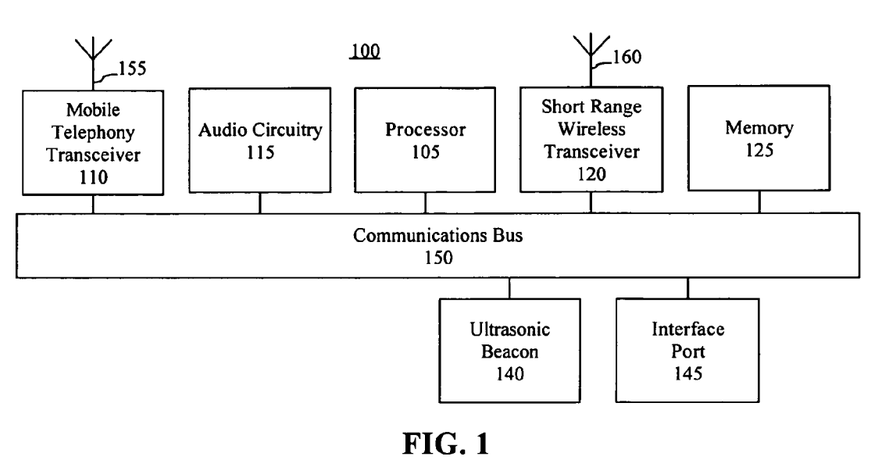
FIG. 1 is a schematic diagram illustrating an embodiment of a mobile communication device (MCD) configured in accordance with the inventive arrangements disclosed herein.

FIG. 1 is a schematic diagram illustrating an embodiment of a mobile communication device (MCD) 100 configured in accordance with the inventive arrangements disclosed herein. As shown, the MCD 100 can include a processor 105, a mobile telephony transceiver 110, audio circuitry 115, a short range wireless transceiver 120, and a memory 125. Each of the aforementioned components can be communicatively linked via a suitable communications bus 150 or other circuitry. For example, the MCD 100 can be implemented as a mobile phone having the features described herein.

The processor 105 can execute a suitable operating system and one or more applications for controlling the various functions of the MCD 100. For example, the processor 105 can execute an operating system that can support the execution of one or more applications intended to run on that platform and which support operation of the various functions and features disclosed herein. As the MCD 100 can include one or more sensors to be described in greater detail herein, the operating system and computing architecture can be designed to support the operation of such sensors. According to one embodiment, the MCD 100 can be compatible with the JAVA 2 Platform, Micro Edition (J2ME®).

The memory 125 can be implemented as random access memory, read-only memory, erasable programmable read-only memory, or any other type of physical memory suitable for use within a mobile communication device, such as the MCD 100. It should be appreciated that the memory 125, while illustrated as a separate component, can be incorporated into the processor 105 or another component. In any case, the memory 125 can include programmatic instructions to be executed by the processor 105 as well as any operational data necessary for operation of the MCD 100.

Wireless signals can be received and sent via the antenna 155 which can be suited for longer-range communications such as conventional cellular or personal communication service (PCS) communications. Accordingly, the antenna 155 can be operatively connected to the mobile telephony transceiver 110. Signals detected by antenna 155 can be provided to the mobile telephony transceiver 110 for processing and decoding. For example, the mobile telephony transceiver 110 can include a codec for coding and decoding information received or to be sent via wireless transmission. The transceiver 110 can make the decoded signals and/or information available to other components of the MCD 100 for processing. Outbound information received by the mobile telephony transceiver 110 can be coded and/or formatted for wireless transmission by the codec and then provided to the antenna 155 for transmission.

Thus, it should be appreciated that the MCD 100 can communicate via conventional cellular telephone and/or PCS telephone calls and access wireless networks, for example using Wireless Access Protocol, or another suitable wireless communications protocol, such that the MCD 100 can access the Internet, the Web, and/or a wide area network, as well as any applications and/or services disposed on such networks via a wireless communications link.

The audio circuitry 115 can include a microphone or other audio input transducer for receiving sound and one or more analog-to-digital converters for digitizing the received sound. The audio circuitry 115 further can include one or more digital-to-analog converters for converting digital information into an analog signal, and one or more analog-to-digital converters for converting an analog signal into a digital format. The audio circuitry 115 can include a speaker or other audio output transducer for generating sound from an analog signal, as well as one or more amplifiers for driving the speaker.

It should be appreciated that the audio circuitry 115 can include additional processors, such as digital signal processors (DSPs) as may be required for processing audio and performing functions such as audio encoding, audio decoding, noise reduction, and the like. According to one embodiment of the present invention, the audio circuitry can be implemented using one or more discrete components. In another arrangement, the audio circuitry 115 can be implemented using one or more integrated circuits configured to perform the various functions disclosed herein. Thus, the MCD 100 can be configured to play various audio formats from streaming formats to MP3's, or other audio file formats such as .wav or .aiff files.

The audio circuitry 115 can also include and/or be communicatively linked to automatic speech recognition (ASR) and synthetic speech generation components that can be used to perform text-to-speech and speech-to-text conversions. When the audio circuitry 115 includes ASR and/or speech generation components, suitable software and/or firmware can be embedded within the audio circuitry 115 and/or be executed by the processor 105. When the audio circuitry 115 is communicatively linked to remotely located ASR and/or speech generation components, communications between the audio circuitry 115 and the remotely located components can occur using the mobile telephony transceiver 110, the short range wireless transceiver 120, the interface port 145, or any other suitable interface.

The MCD 100 also can include a short range wireless transceiver 120 as well as an antenna 160 operatively connected thereto. The short-range wireless transceiver 120 can both send and receive data. For example, according to one embodiment of the present invention, the short range wireless transceiver 120 can be implemented as a Blue-Tooth-enabled wireless transceiver, or as a transceiver configured to communicate via one of the 802.11 family of short range wireless communications specifications. The short range wireless transceiver 120 and accompanying antenna 160 can be configured to communicate using any of a variety of short range, wireless communications protocols and/or systems. Through the short range wireless transceiver 120, the MCD 100 can communicate with a local area network, or other short range wireless network. Still, the various examples disclosed herein have been provided for purposes of illustration only and should not be construed as limitations of the present invention.

The MCD 100 further can include an ultrasonic beacon 140. The ultrasonic beacon 140 or transponder can be detected by one or more ultrasonic transceivers referred to as pilots or monitors. The pilot devices can be dispersed throughout a room or other environment, known as a "smart" environment, to detect the location of the MCD 100, or any other device having one or more such ultrasonic beacons 140.

It should be appreciated, however, that the present invention is not limited to the use of ultrasonic beacons as a means of determining location. Rather, any suitable technology can be used. For example, the MCD 100 can be equipped with a Global Positioning System receiver or other satellite-based location detection system. In another example, the MCD 100 can include a radio-frequency-based location detection system such as one utilizing radio-frequency identifier tags or another radio-frequency beacon.

The MCD 100 can also include one or more interface ports 145 used to physically connect devices and/or peripherals to the MCD 100. For example, the interface port 145 can be a standard wall jack to initiate telephone calls over the Public Switched Telephone Network (PSTN). The interface port 145 can also include a universal serial bus (USB) port, a firewire (IEEE 1394) port, a parallel port, a serial port, an Ethernet port, an audio port, or the like. Use of the interface port 145 for communicatively linking the MCD 100 with external devices can be advantageous in situations where wireless connectivity may not be available, is intermittent, or otherwise unsuitable for a particular purpose.

Each of the various components of the MCD 100 disclosed herein can be communicatively linked with one another using appropriate circuitry, whether through the memory 125, one or more additional memories (not shown), the processor 105, one or more additional interface processors or logic controllers (not shown), and/or the communications bus 150. One skilled in the art will recognize that the components disclosed herein can be embodied in other forms and that the configuration disclosed and described with reference to FIG. 1 is provided for purposes of illustration only. For example, the components can be implemented as one or more discrete components, as one or more processors, logic controllers, DSPs, or any combination thereof.

Figure 2:
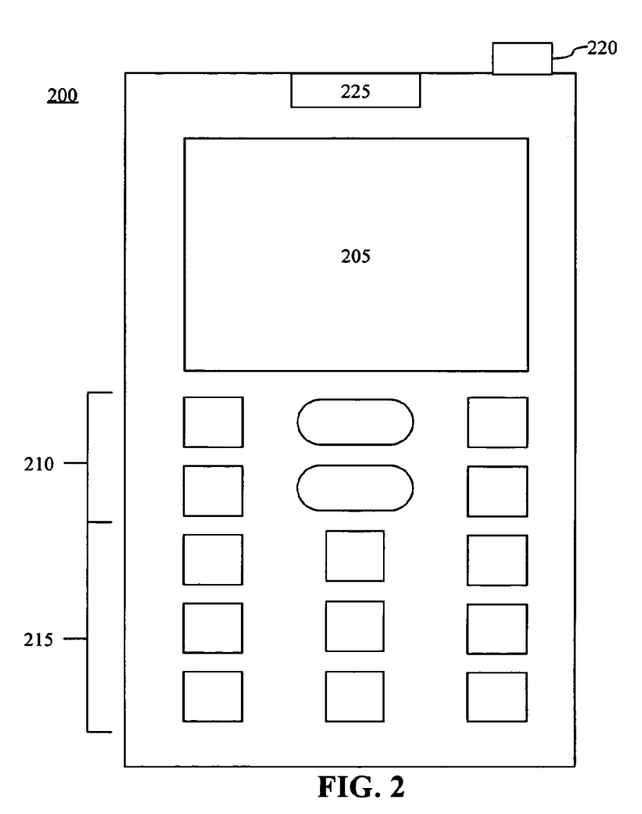
FIG. 2 is a schematic diagram illustrating an embodiment of an MCD in accordance with the inventive arrangements disclosed herein.

FIG. 2 is a schematic diagram illustrating an embodiment of an MCD 200 in accordance with the inventive arrangements disclosed herein. As shown, the MCD 200 can include a display 205, one or more control or operational keys 210, which can include special function command keys for operation of one or more of the functions disclosed herein, alphanumeric keys or buttons 215, and an antenna 220 (which may be configured to be fully located within the MCD 200). The MCD 200 further can include a battery or other power source (not shown). Notably, the MCD 200 can include a rechargeable battery as well as additional power sources to enable the MCD 200 to be active for extended periods of time.

The physical arrangement of the MCD 200 has been provided for purposes of illustration only. As such, it should be appreciated that the various components can be located in any of a variety of different configurations. For example, the MCD 200 can include additional keys or controls disposed on the frontal portion or the sides of the unit.

According to one embodiment of the present invention, the physical arrangement of the MCD 200 can be conducive for use by visually impaired individuals or those that may have difficulty accessing and/or operating the keys and/or controls of conventional mobile computing devices, such as the elderly, persons with physical disabilities, or other infirmities. For example, the control keys 210 and the alphanumeric keys 215 of the MCD 200 can be larger in size than conventional mobile device keys and can be spaced a greater distance from one another with respect to both the width and length of the MCD 200. That is, the horizontal key spacing and the vertical key spacing can be greater than that found with conventional mobile devices. Further, the control keys 210 can include Braille markings for key identification purposes.

The MCD 200 can include a display 205, such as a liquid crystal display (LCD) implemented in either grayscale or color, a touch screen, or any other type of suitable display screen. The display 205 can be larger than those found on conventional mobile computing devices and can have an increased contrast ratio if so desired.

As noted, the MCD 200 can include a variety of sensors. As shown in FIG. 2, the MCD 200 can be configured with one or more location detection mechanisms 225. While the location detection mechanism 225 can be positioned on the MCD 200 in any of a variety of different locations, according to one embodiment, the location detection mechanism 225 can be positioned at the top portion of the MCD 200. Other sensors can be located throughout the exterior portion of the MCD 200.

Figure 3:
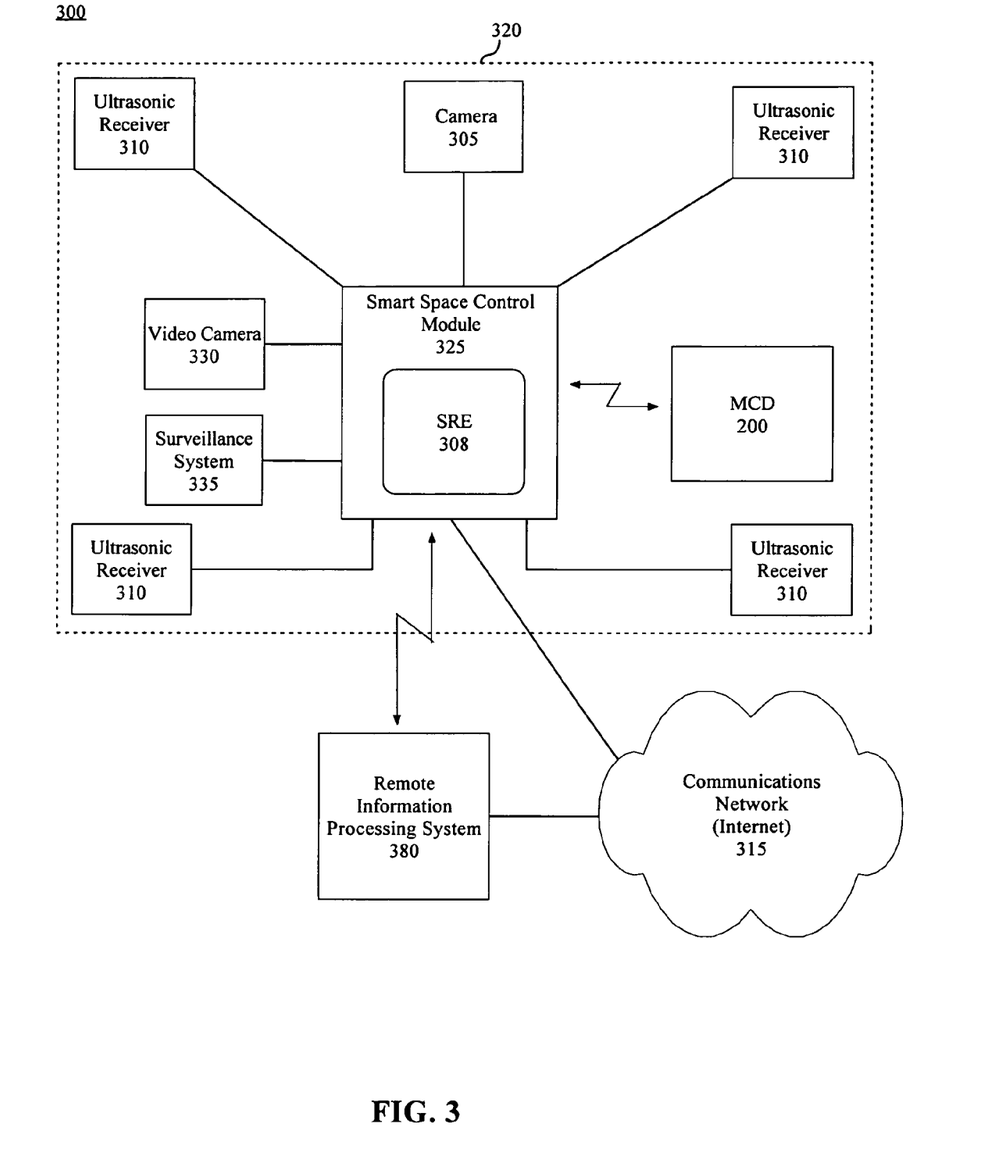
FIG. 3 is a schematic diagram illustrating a system within which an MCD can be utilized in accordance with another embodiment of the present invention.

FIG. 3 is a schematic diagram illustrating a system 300 within which an MCD 200 can be utilized in accordance with another embodiment of the present invention. It should be appreciated that the MCD 200 can be configured to operate in a variety of environments, including indoor and outdoor environments. FIG. 3 depicts a smart space 320, which can be a customized environment equipped with suitable transceivers, communications equipment, and other controller units. For example, a home can be so configured. Alternately, a workspace, caretaking facility, building, park, mall, and/or other space that can be occupied and/or inhabited by persons can be configured as a smart space. In one embodiment, the MCD 200 can interact within smart space 320. In another embodiment, the MCD 200 can operate within a standard environment that has not been specifically modified for the needs of a physically and/or mentally challenged person or other MCD 200 user.

The MCD 200 can communicate with a smart space control module (SSCM) 325. The SSCM 325 can include a server disposed within a computing device, such as a personal computer, a laptop, or other information processing appliance that can be communicatively linked to the MCD 200. The MCD 200 can also communicate, via the SSCM 325, with components shown as being linked to the SSCM 325, such as at least one of a video camera 330, at least one of an ultrasonic receiver 310, at least one of a camera 305, a surveillance system 335, or the like.

The MCD 200 can include one or more application programs that allow the user to access the functionality of the various systems and/or devices connected to the SSCM 325. In one embodiment, the MCD 200 can include a thin client and the SSCM 325 can function as an application server. The SSCM 325 can also be configured such that information exchanged between the MCD 200 and the SSCM 325 can be tailored for the needs, capabilities, and privileges of different users and/or MCDs.

It should be appreciated that the MCD 200 can communicate with the SSCM 325 using any of a variety of different communications mechanisms and that the MCD 200 is not limited to any specific communication mechanism. For example, the MCD 200 can initiate mobile telephone and/or conventional telephone calls to the SSCM 325 when the MCD 200 is not located within or proximate to the home within which the SSCM 325 is disposed. In another example, the MCD 200 can communicate with the SSCM 325 using short-range wireless communications when in range. In still another example, the MCD 200 can be linked to the SSCM 325 via one or more interface ports, or via the Internet.

In one aspect of the present invention, the location of the MCD 200 can be determined by the system 300. As shown, the ultrasonic receivers 310, which can be dispersed throughout a room or building, can detect a beacon signal emitted from the ultrasonic beacon disposed within the MCD 200. Information collected by the ultrasonic transceivers 310 can be provided to the SSCM 325 for processing such that the SSCM 325 can determine the location of the MCD 200 within the smart space. In another embodiment, a user can wear a jacket, vest, or other piece of clothing outfitted with one or more such beacons, for example on each shoulder. Such an arrangement allows the SSCM 325 to detect not only the location of a user, but also the orientation of the user. The position of the beacon(s), whether within the MCD 200 or a piece of clothing, can be calculated based upon the time required by the ultrasonic waves to reach each receiver. A trilateration technique also can be used.

Still, as noted, any of a variety of location detection mechanisms can be used. For example, digital image processing using one or more video cameras 330, sound, and/or motion detection technology, for example from the surveillance system 335, can be used to determine the location of a user. In the case where GPS or other satellite technology is used, the MCD 200 can determine its own location. Accordingly, such information can be sent to the SSCM 325 through any of the aforementioned communication techniques.

Using the location detection mechanisms described herein, the SSCM 325 can determine the location of the MCD 200, and therefore the user since the MCD 200 is designed to be on or close to the body of the user. Based on the input from the location detection mechanisms, the SSCM 325 can orient at least one camera 305 in the direction of the MCD 200 in order to continually monitor the movements of the user as the user moves about within the smart space.

FIG. 3 also shows a remote information processing system 380 communicatively linked to the SSCM 325. Similar to the MCD 200, the remote information processing system 380 can communicate with the SSCM 325 using any of a variety of different communications mechanisms. For example, the remote information processing system 380 can initiate mobile telephone and/or conventional telephone calls to the SSCM 325. Additionally, the remote information processing system 380 can communicate to the SSCM 325 via the Internet. It should be appreciated that the remote information processing system 380 can be a mobile communication device, a personal computer, or other device capable of being communicatively linked to the SSCM 325.

In another aspect of the present invention, the SSCM 325 can be configured to execute a Speech Recognition Engine (SRE) 308. SRE 308 can be a software application executing within the SSCM 325. In one embodiment, a spoken utterance can be received within the MCD 200. Accordingly, the MCD 200 can be configured to send the spoken utterance to the SSCM 325 for analysis via the SRE 308. The spoken utterance can be converted to text and parsed to locate words which indicate that the user requires immediate assistance, such as "HELP", or "EMERGENCY." Upon determining that the user is requesting immediate assistance from a remote caregiver, the SSCM 325 can transmit the "help" request to the remote information processing system 380. It should be appreciated by one skilled in the art that the MCD 200 can also contain a control mechanism, such as a button, for the user to alert the caregiver in a nonverbal fashion.

In one embodiment, an application within the remote information processing system 380 can allow a caregiver to communicate with the SSCM 325 in order to request a picture of the user. Upon receiving the request, the SSCM 325 can transmit a command to the camera 305 to capture an image of the area surrounding the MCD 200. Accordingly, the SSCM 325 can send the resulting picture to the remote information processing system 380. In one embodiment, the remote information processing system 380 can be configured to request a picture of the user in response to a user "help" request. As described herein, upon determining that a user utterance received within the MCD 200 is a "help" request, the SSCM 325 can be configured to notify the remote information processing system 380. In another embodiment, the remote information processing system 380 can be configured to request a picture of the user at any time in order to make a routine status check of the user's condition. It should be appreciated by one skilled in the art that the MCD 200 device can also contain a photographic mechanism for capturing an image of the user for display on the remote information processing system 380.

System 300 can also include a communications network 315. The network can communicatively link to the MCD 200, for example via a mobile communications link. The network 315 can also communicatively link the SSCM 325 and the remote information processing system 380. The communications network 315 is depicted as an Internet network. It should be appreciated by those skilled in the art, however, that communications network 315 can also include a wide area network, the public switched telephone network (PSTN), a wireless communications network such as a mobile network, or other data network.

It should also be appreciated that a remote agent, such as a caregiver, can view the movements of the user in real-time by accessing the camera 305 directly via the Internet using a web browser (not shown).

Figure 4:
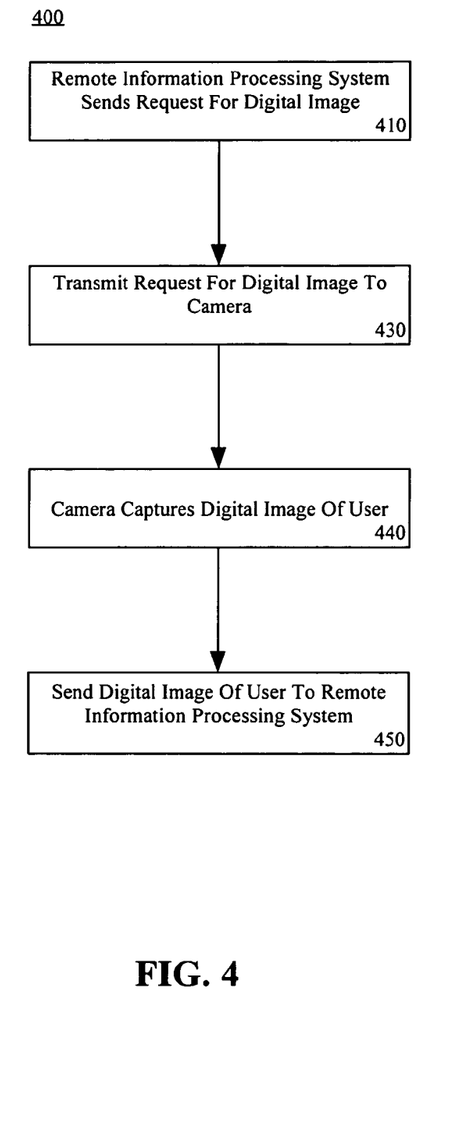
FIG. 4 is a flow chart illustrating a method of sending a digital image of the user to a caregiver, in accordance with one embodiment of the present invention.

FIG. 4 is a flow chart illustrating a method 400 in accordance with one embodiment of the present invention. The method 400 can be used to send a picture of the user to the remote information processing system. Notably, the location of the MCD within the smart space can be automatically determined using any of the location detection mechanisms described herein. Based on the input from a location detection mechanism, the SSCM can orient at least one camera in the direction of the MCD at all times in order to continually track or "follow" the movements of the MCD within the smart space.

The method 400 can begin in step 410 where a request for a picture or an image of the user is sent by the remote information processing system. As discussed herein, the remote information processing system can be configured to initiate the request upon notification by the SSCM that the user requires assistance. The remote MCD can also be configured to initiate a request anytime that the remote agent, such as a caregiver, desires to check on the status of the user.

In step 430, upon receiving the request for an image of the user, the SSCM can transmit the request to at least one camera. In step 440, the camera, which can be oriented in the direction of the MCD, can capture a digital image of the MCD and the surrounding area and forward the digital image to the SSCM. In step 450, the SSCM can transmit the digital image to the remote information processing system. Assuming that the MCD is being carried by the user or is otherwise attached or close to the user, the picture sent to the remote information processing system can include an image of the user. Notwithstanding, as noted, the location of the user can also be determined via one or more beacons integrated into a jacket, vest, or other piece of clothing worn by the user.

Figure 5:
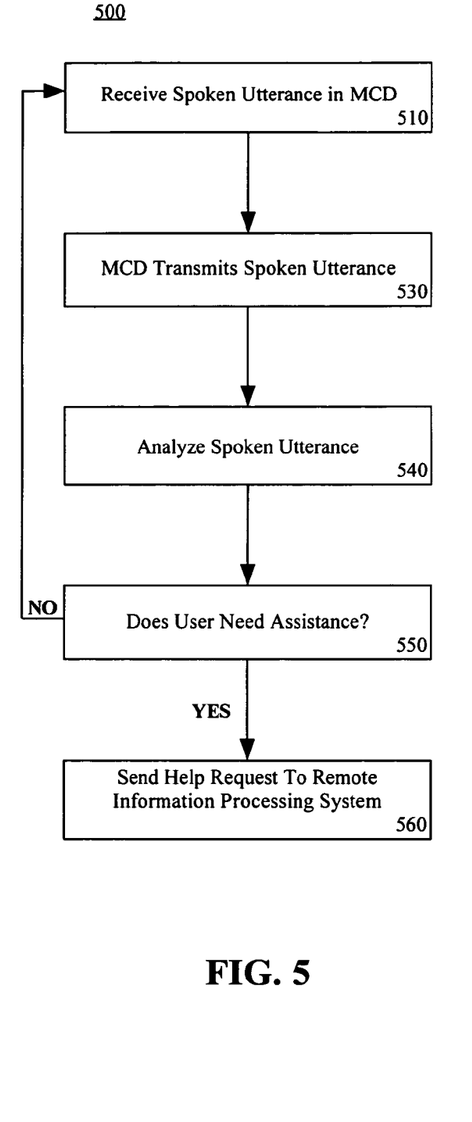
FIG. 5 is a flow chart illustrating a method of sending a help request to a remote information processing system, in accordance with another embodiment of the present invention.

FIG. 5 is a flow chart illustrating a method 500 in accordance with another embodiment of the present invention. The method 500 can be used to determine whether the user is requesting assistance from a remote agent, such as a caregiver. The method can begin in step 510 where the MCD receives a spoken utterance. In step 530, the MCD can transmit the spoken utterance to the SSCM for analysis.

In step 540, the SSCM can analyze the spoken utterance using a speech recognition system. The spoken utterance can be converted to text and parsed to locate words which indicate that the user requires assistance, such as the words "HELP", "EMERGENCY", or some other keyword or phrase. The user can also request assistance by activating controls on the MCD, such as buttons, in order to send a help signal to the SSCM.

In step 550, if the SSCM determines that the user does not need assistance, then the method 500 can loop back to step 510 and wait for another spoken utterance. If, however, the SSCM determines that the user is requesting assistance, the method 500 can proceed to step 560 where the SSCM can send a "help" request to a remote information processing system for presentation to a remote agent, such as a caregiver. It should be appreciated that a "help" request can be presented to the caregiver via the remote information processing system in an audible as well as a visual format.

The present invention can be realized in hardware, software, or a combination of hardware and software. The present invention can be realized in a centralized fashion in one computer system or in a distributed fashion where different elements are spread across several interconnected computer systems. Any kind of computer system or other apparatus adapted for carrying out the methods described herein is suited. A typical combination of hardware and software can be a general-purpose computer system with a computer program that, when being loaded and executed, controls the computer system such that it carries out the methods described herein.

The present invention also can be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention can be embodied in other forms without departing from the spirit or essential attributes thereof. Accordingly, reference should be made to the following claims, rather than to the foregoing specification, as indicating the scope of the invention.

What is claimed is:

1. A method of remote surveillance and assisted care using a mobile communication device, the method comprising the steps of:
   determining a location of a user;
   adjusting at least one camera according to the location;
   capturing an image of an area around the location;
   transmitting the image to a remote information processing system;
   receiving within the mobile communication device a spoken utterance;
   transmitting the spoken utterance to a voice recognition engine, and converting the utterance received by the voice recognition engine into text;
   identifying at least a portion of the text as a help request; and
   transmitting the help request to the remote information processing system.

2. The method of claim 1, said transmitting step comprising transmitting the spoken utterance over a short range wireless network.

3. The method of claim 1, further comprising:
   prior to said step of determining a location; receiving from the remote information processing system a status request to view said image.

4. A system for providing remote surveillance, comprising:
   a location tracking mechanism;
   a mobile communication device configured to interact with the location tracking mechanism;
   a server in communication with the location tracking mechanism and the mobile communication device;
   at least one adjustable camera, wherein said server controls the orientation of the camera based upon information from the location tracking system; and
   a voice recognition engine wherein said server receives a user utterance from the mobile communication device, and converts the user utterance into text.

5. The system of claim 4, wherein the server identifies the user utterance as a request for help and responsively contacts a caregiver.

6. The system of claim 4, wherein the voice recognition engine is disposed within a personal computer.

7. The system of claim 4, wherein the server obtains an image from said at least one adjustable camera and transmits the image to a remote information processing system.

8. A machine readable storage, having stored thereon a computer program having a plurality of code sections executable by a machine for causing the machine to perform the steps of:

determining a location of a user;
adjusting at least one camera according to the location;
capturing an image of an area around the location;
transmitting the image to a remote information processing system;
receiving within the mobile communication device a spoken utterance;
transmitting the spoken utterance to a voice recognition engine, and converting the utterance received by the voice recognition engine into text;
identifying at least a portion of the text as a help request; and
transmitting the help request to the remote information processing system.

9. The machine readable storage of claim 8, said transmitting step comprising transmitting the spoken utterance over a short range wireless network.

10. The machine readable storage of claim 8, further comprising:
prior to said step of determining a location; receiving from the remote information processing system a status request to view said image.

* * * * *